United States Patent [19]

Wagnières et al.

[11] Patent Number: 5,219,346

[45] Date of Patent: Jun. 15, 1993

[54] LIGHT DIFFUSER FOR THE PHOTODYNAMIC THERAPY OF TUMORS IN THE OESOPHAGUS OF A PATIENT

[75] Inventors: Georges Wagnières, Lutry; Hubert van den Bergh, Goumoens-la-Ville; Philippe Monnier, Lausanne, all of Switzerland

[73] Assignee: Ciba-Geigy Corporation, Ardsley, N.Y.

[21] Appl. No.: 638,249

[22] Filed: Jan. 4, 1991

[30] Foreign Application Priority Data

Jan. 9, 1990 [CH] Switzerland .................... 60/90

[51] Int. Cl.$^5$ ............................................... A61B 17/36
[52] U.S. Cl. .......................................... 606/16; 606/2; 606/13; 606/17; 606/18
[58] Field of Search ............... 606/2, 7, 13–18, 606/27; 128/395–398

[56] References Cited

U.S. PATENT DOCUMENTS

| | | |
|---|---|---|
| 4,017,150 | 4/1977 | Imai . |
| 4,311,142 | 1/1982 | Machida ............... 606/12 |
| 4,336,809 | 6/1982 | Clark ................... 128/398 |
| 4,551,129 | 11/1985 | Coleman et al. . |
| 4,558,093 | 12/1985 | Hatzenbuhler et al. ........... 606/2 |
| 4,660,925 | 4/1987 | McCaughan, Jr. . |
| 4,693,244 | 9/1987 | Daikuzono . |
| 4,693,556 | 9/1987 | McCaughan, Jr. . |
| 4,736,743 | 4/1988 | Daikuzono ............... 606/17 |
| 4,860,743 | 8/1989 | Abela ..................... 606/7 |
| 4,913,142 | 4/1990 | Kittrell et al. ............. 606/15 |
| 4,927,426 | 5/1990 | Dretler ................. 604/280 |
| 5,071,417 | 12/1991 | Sinofsky ................ 606/10 |
| 5,151,096 | 9/1992 | Khoury .................. 606/7 |

FOREIGN PATENT DOCUMENTS 2154761 9/1985 United Kingdom .

OTHER PUBLICATIONS

Wagnières et al., Photodynamic Therapy of Early Cancer in the Upper Aerodigestive Tract & Bronchi, 1990, pp. 251–252, FIGS. 1 & 2; p. 258 FIG. 10.
Merck Index 11th Edition 1989, pp. 1207 & C1286.

Primary Examiner—Randall L. Green
Assistant Examiner—A. Zuttarelli
Attorney, Agent, or Firm—Irving M. Fishman; Karen G. Kaiser; Barbara J. Ikeler

[57] ABSTRACT

A light diffuser for simultaneous photodynamic therapy and hyperthermic treatment in the oesophagus has an arrangement (14 to 18) which disperses radially the light (10) fed in by way of an optical fiber (6) and has a tube (12) filled with silicone to which are added concentrations, modulated in the axial direction, of quartz grains having a diameter of approximately 40 μm which bring about a refraction having little dependence on the wavelength.

11 Claims, 1 Drawing Sheet

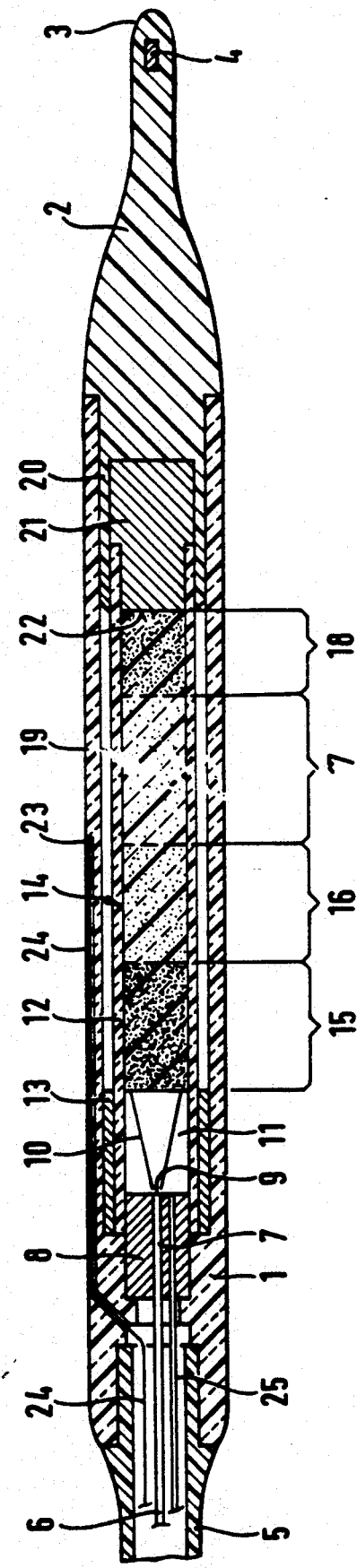

LIGHT DIFFUSER FOR THE PHOTODYNAMIC THERAPY OF TUMORS IN THE OESOPHAGUS OF A PATIENT

The invention relates to a light diffuser for the photodynamic therapy of tumours in the oesophagus of a patient, which diffuser has an optical fibre for feeding laser light into a tube which deflects the axially incident light radially and contains particles embedded in a composition and which has a mirror at the front end, arranged opposite the optical fibre, and is arranged coaxially in a sleeve-shaped probe housing.

A light diffuser of that type is known from Hubert van den Bergh, Light and porphyrins in cancer therapy, Chemistry in Britain, May 1986, Vol. 22, No. 5 and has at its front end a Savary-Gillard dilator permitting the gentle introduction of the probe housing which has a diameter of approximately 20 mm and an overall length of approximately 75 mm. The sleeve-shaped probe housing consists of PMMA and is connected to the front end of a nylon pipe provided with distance markings. The optical fibre extends through the lumen of the nylon pipe and terminates inside the probe housing at a short distance from the tube which disperses the light in a radial direction. The tube consists of PTFE and is filled with epoxy resin to which $TiO_2$ particles have been added at a concentration of from 0.1 to 1%. The first portion, which is closest to the optical fibre, has an intermediate concentration of 0.5% $TiO_2$. The middle portion of the tube has a concentration of 0.1% and the final portion a concentration of 1% $TiO_2$ particles. The diameter of the particles is 0.2 µm so that, in the case of a light wavelength of the same order or magnitude, a Debye scattering results which is greatly wavelength-dependent.

This problem is solved according to the invention in diffuser of the type mentioned at the beginning that is resistant to aging and permits as homogeneous a dosage as possible of the radiation required for photodynamic therapy and of the longer-wave radiation required for hyperthermic treatment.

The problem is solved according to the invention in that the particles deflecting the light are grains that have a large diameter relative to the light wavelength and have a refractive index that differs from the refractive index of the composition.

In a preferred embodiment of the invention, the grains are quartz grains having a diameter of approximately 40 µm and the composition consists of silicone.

In order to obtain as homogeneous as possible a light distribution in the oesophagus, the tube is constructed in the axial direction in successive portions having different concentrations of quartz grains. The first portion, which is struck directly by the laser light, has a greater concentration of quartz grains than have the portions following in the axial direction towards the front end.

The first portion, which has a high concentration of quartz grains, is preferably adjoined in the axial direction by at least one portion having a relatively low concentration of quartz grains, and that portion is adjoined in the axial direction by a final portion having an intermediate concentration of quarts grains.

It is especially advantageous if two portions having a very low and a low concentration of quartz grains are provided as the middle region between the first portion and the final portion.

In order to be able to effect a controlled hyperthermic treatment, a thermoelement which is connected to a thermal monitoring device is provided in the surface of the probe housing.

In addition to the optical fibre provided for feeding in light, it is preferable to provide a light-monitoring fibre, the end face of which is arranged in a laterally offset manner near the optical fibre and is struck by some of the light returning from the rear end of the tube. The light-monitoring fibre is connected to a light-intensity control and monitoring device and accordingly enables the photodynamic therapy to be monitored and controlled accurately.

An embodiment of the invention is described in detail hereinafter with reference to the drawing which shows, in a single FIGURE, the light diffuser according to the invention which permits simultaneous photodynamic therapy and hyperthermic treatment in the oesophagus.

The light diffuser shown in the drawing has a sleeve-shaped probe housing 1 which is in the form of a PMMA cylinder having an outside diameter of from 15 to 18 mm and an overall length of approximately from 77 to 117 mm. As is shown in the drawing, the front end, shown on the right in the drawing, is connected to a Savary-Gillard dilation member 2 which has the rounded shape, shown in the drawing, ending in a tip 3, which enables the light diffuser to be introduced gently into the oesophagus of a patient who is suffering from a tumour and who is to be treated by means of photodynamic therapy.

In order to be able to observe the position of the light diffuser in an X-ray image, an X-ray marker 4 is provided near the tip 3.

The rear end of the probe housing 1 is connected to a nylon pipe 5 which has length markings (not shown in the drawing) on its surface in order to enable the depth of insertion of the light diffuser to be monitored. Running through the inside of the nylon pipe 5 is an optical fibre 6 which is struck at the feed-in end (not shown in the drawing) by the light of a laser. For photodynamic therapy, a laser having a light wavelength of 0.630 µm can be provided. In the case of therapy by hyperthermia, laser light having a wavelength of, for example, 1.064 µm is fed into the optical fiber 6. It is known that light of this longer wavelength penetrates deeper into the tissue of a patient and can be used for relatively homogeneous heating.

The front end 7 of the optical fiber 6 is secured in a holding member 8, locked in the probe housing 1 in such a manner that it is axially immovable, through which member it extends coaxially. The end face 9 of the optical fibre 6 is approximately flush with the end face facing to the right in the drawing of the holding member 8 and emits a widening beam 10 which traverses a cavity 11 in the direction towards the front end of the light diffuser.

As can be seen in the drawing, there is arranged inside the probe housing 1 a tube 12 of PTFE which runs coaxially with respect to the probe housing 1 and in the rear end of which, on the left in the drawing, the holding member 8 engages. The rear region of the tube 12 is surrounded by an aluminium ring 13, the inner surface of which reflects impinging light. The aluminium ring 13 extends in the direction towards the front end of the tube approximately up to the position where the widening beam 10 impinges on a silicone filling 14 in the tube 12. At that position, the widening beam 10 has reached its greatest diameter, which is slightly smaller than the inside diameter of the tube 12. The silicone filling 14 contains quartz grains or quartz particles having a diameter of 40 μm. The quartz grains embedded in the silicone filling 14 bring about refraction as a result of the bending of the incident light at the transition between the quartz and the silicone, which is caused by the differing refractive indices of those materials. This refraction is wavelength-dependent to only a relatively slight degree, so that the silicone filling 14 interspersed with quartz grains can disperse in a radial direction light entering axially into the tube 12 in a manner that is only slightly wavelength-dependent.

The tube 12 arranged concentrically in the probe housing 1 preferably has a silicone filling 14 having quartz grain concentrations that differ in the axial direction.

In a first portion 15, which is approximately 12 mm long, there is a high concentration of quartz grains, it being possible for the concentration to be approximately 0.3% by weight.

Adjoining the first portion 15 is a second portion 16 which is 11 mm long and has a low quartz grain concentration of approximately 0.1% by weight. A following third portion 17 which is 14 mm long likewise has a, relatively, very low quartz grain concentration of approximately 0.06% by weight. In a fourth portion 18 which is 8 mm long, the silicone filling 14 contains quartz particles having a diameter of 40 μm and an intermediate concentration of approximately 0.25% by weight. Such a distribution of concentration in the axial direction results in a very high degree of homogeneous light dosage in the patient's oesophagus, both shortwave light of photodynamic therapy and longer-wave light for hyperthermic treatment being well dispersed. It is advantageous that the silicone has a high degree of transparency and good ageing stability.

Between the outer surface of the tube 12 and the inner surface of the probe housing 1 is an annular space 19 which extends between the aluminium ring 13 and a front closing member 20.

Projecting into the front end of the tube 12 is an aluminium cylinder 21, of which the end face 22 facing to the left in the drawing is in the form of a mirror and contributes to the homogenisation of the light distribution.

In the middle region of the probe housing 1 and in the surface thereof is a very small thermoelement 23 casting only a small shadow, which is largely compensated for by the diffusion of the light diffuser and the irradiated tissue. The thermoelement 23 is connected by way of a line 24 to a thermal monitoring device, which is not shown in the drawing. A light-intensity control and monitoring device, which is likewise not shown in the drawing, is connected to a light-monitoring fibre 25 which, like the line 24 and the optical fibre 6, extends through the nylon pipe 5 and terminates with its end face in the vicinity of the end face 9 of the optical fibre 6. The light-monitoring fibre 25 thus makes it possible to monitor and control the intensity of the light in the cavity 11 and accordingly to monitor and control the light intensity used to irradiate the patient.

The probe housing 1 may a have a reflective metal coating on its inside along half its circumference in order thus to ensure that the light diffuser emits light in the radial direction not over 360 degrees but only over 180 degrees. The reflective metal coating may be applied directly to the inside of the probe housing 1 or to an additional part which is introduced into the annular space 19 and is provided with a reflective metal coating in the shape of a trough.

Instead of the above-mentioned quartz grains, it is possible to use other transparent grains having a refractive index that differs from the refractive index of the silicone. In particular, the grains, which have a diameter of approximately 40 μm, may consist of glass, aluminium oxide, barium fluoride, calcium fluoride and flint glass.

Instead of silicone, it is possible to use other plastics or compositions having suitable transparency and stability properties.

What is claimed is:

1. A light diffuser for photodynamic therapy of a tumor in an oesophagus of a patient, said diffuser comprising
   (a) a tube having a front portion and a rear portion;
   (b) an optical fiber for feeding laser light of a specified wavelength axial into said tube through said rear portion toward said front portion;
   (c) composition, including quartz grains embedded therein, contained within said tube between said rear portion and said front portion, said composition having a first refractive index and said quartz grains having a second refractive index different from said first refractive index, wherein said quartz grains have a large diameter relative to said specified wavelength of the laser light, said composition having a plurality of different regions including at least a first region and a final region arranged axially, with said final region of said plurality of regions proximal to said front portion of said tube, wherein said quartz grains embedded in the composition are of different concentrations in the different regions;
   (d) a mirror located within said tube between said composition and said front portion opposite said optical fiber; and
   (e) a sleeve-shaped probe housing wherein said tube, fiber, composition and mirror are arranged coaxially such that the laser light is deflected radially outward from said probe housing.

2. The light diffuser of claim 1, wherein the diameter of the quartz grains is approximately 40 μm.

3. The light diffuser of claim 1, wherein the composition in said first region is struck directly by said laser light and wherein the concentration of quartz grains in the first region is higher than the concentration of quartz grains in the plurality of regions of the composition.

4. The light diffuser of claim 3, wherein the plurality of regions includes an intermediate region containing a low concentration of said quartz grains, said intermediate region being located between said first region and said final region, and wherein said final region has a concentration of quartz grains less than the concentration of the first region and more than the concentration of the intermediate region.

5. The light diffuser of claim 4, wherein the plurality of regions further includes an additional region situated between said first region and said intermediate region, and wherein the additional region has a concentration of quartz grains less than the concentration of the intermediate region.

6. The light diffuser of claim 1, wherein said probe housing has a surface and a thermoelement is provided in said surface.

7. The light diffuser of claim 6, wherein said thermoelement is connected to a thermal monitoring device.

8. The light diffuser of claim 1, further comprising a light-monitoring fiber having an end face, said end face being arranged in a laterally offset manner near said optical fiber and wherein said light-monitoring fiber is situated inside the sleeve-shaped probe housing and outside the front portion of the tube such that the light-monitoring fiber is contacted by the laser light before the laser light is deflected radially outward from the probe housing.

9. The light diffuser of claim 8, wherein said light-monitoring fiber is connected to a light-intensity control and monitoring device.

10. The light diffuser of claim 1, wherein said composition includes silicone.

11. The light diffuser of claim 10, wherein said composition consists essentially of silicone and quartz grains embedded therein.

* * * * *